United States Patent
Price et al.

(10) Patent No.: US 6,900,247 B2
(45) Date of Patent: May 31, 2005

(54) NATURAL GAS CONVERSION TO HYDROCARBONS AND AMMONIA

(75) Inventors: Julian Graham Price, Vanderbijlpark (ZA); Barry Antony Tindall, Sasolburg (ZA)

(73) Assignee: Sasol Technology (Proprietary) Limited, Rosebank (ZA)

( * ) Notice: Subject to any disclaimer, the term of this patent is extended or adjusted under 35 U.S.C. 154(b) by 412 days.

(21) Appl. No.: 10/056,232

(22) Filed: Jan. 25, 2002

(65) Prior Publication Data

US 2002/0143219 A1 Oct. 3, 2002

Related U.S. Application Data

(63) Continuation of application No. PCT/ZA00/00125, filed on Jul. 25, 2000.

(30) Foreign Application Priority Data

Jul. 29, 1999  (ZA) ................................................ 99/4879

(51) Int. Cl.[7] ............................. C07C 27/00; C01C 1/04
(52) U.S. Cl. ....................... 518/702; 518/700; 518/703; 518/704; 518/705; 518/726; 423/359
(58) Field of Search ................................. 518/700, 702, 518/703, 704, 705, 726; 423/359

(56) References Cited

U.S. PATENT DOCUMENTS

| | | | |
|---|---|---|---|
| 2,494,561 A | * 1/1950 | Kemp, Jr. ................... | 423/363 |
| 4,666,680 A | 5/1987 | Lewis ......................... | 422/191 |
| 4,886,651 A | * 12/1989 | Patel et al. ................... | 423/359 |
| 5,023,276 A | 6/1991 | Yarrington et al. .......... | 514/703 |
| 5,245,110 A | 9/1993 | Van Dijk et al. ............ | 585/946 |
| 5,543,437 A | * 8/1996 | Benham et al. ............. | 518/700 |
| 6,248,794 B1 | 6/2001 | Gieskes ...................... | 518/700 |

FOREIGN PATENT DOCUMENTS

| | | |
|---|---|---|
| EP | 0342610 | 11/1989 |
| EP | 0770578 | 5/1997 |

* cited by examiner

*Primary Examiner*—J. Parsa
(74) *Attorney, Agent, or Firm*—Ladas & Parry LLP

(57) ABSTRACT

A process for the production of hydrocarbons and ammonia, and more particularly a process for optimizing the production of hydrocarbons and ammonia using a combined hydrocarbon synthesis plant and ammonia synthesis plant. Synthesis gas exiting a reforming section of the hydrocarbon synthesis process is sent to a hydrogen extraction unit, where it is divided into a hydrogen-rich stream and a hydrogen-poor stream. The hydrogen-rich stream is then fed into an ammonia synthesis process. The hydrogen-poor stream may be returned to the hydrocarbon synthesis process or may be used as a fuel gas. The process reduces emission of $CO_2$ into the atmosphere, and requires only one reforming section and one air separation unit for both processes. Removal of hydrogen from the hydrocarbon synthesis process before the synthesis gas enters a Fischer-Tropsch reactor also lowers the $H_2/CO$ ratio of the synthesis gas, therefore resulting in better hydrocarbon selectively.

9 Claims, No Drawings

NATURAL GAS CONVERSION TO HYDROCARBONS AND AMMONIA

This application is a continuation International Application PCT/ZA00/00125 filed on Jul. 25, 2000, which designated the U.S.

The present invention relates to a process for the production of hydrocarbons and ammonia, and more particularly to a process for the optimisation of the production of hydrocarbons and ammonia using a combined Fischer-Tropsch process plant and ammonia synthesis plant.

In the specification and claims which follow, the term "synthesis gas" is intended to refer to a gas containing predominantly CO and $H_2$ which is intended to be used to manufacture liquid hydrocarbons. Unless it is apparent from the context, the term is not intended to refer to a gas used to manufacture ammonia.

BACKGROUND OF THE INVENTION

Ammonia is the second largest chemical synthetic product with approximately 400 ammonia plants operating globally. $H_2$ and $N_2$ are reacted at a temperature of between 400 and 500° C. and a pressure greater than 100 bar over an iron based catalyst The production of the nitrogen and the hydrogen is the single most expensive step in the synthesis process. Much effort has hence been devoted to reducing the cost of synthesis gas production. Liquified Petroleum Gas (LPG), naphtha, petroleum coke, coal and natural gas have been used as feedstocks, although the vast majority of processes utilise natural gas as feedstock and fuel. CO, $CO_2$ and $H_2O$ are all considered poisons for the catalyst even at parts per million concentration levels and hence great effort is made to remove them from the synthesis gas. Sulphur, particularly in the form of $H_2S$ also acts as a permanent poison and has to be removed from the synthesis gas to very low levels.

State of the art ammonia synthesis processes use a two step reforming process. The primary reformer is an indirectly heated tubular reactor filled with a Ni catalyst The natural gas is passed through this reactor after being mixed with steam. The reaction is controlled so that there is about 15% methane remaining in the exit stream. The partly reformed gas is then transferred to the secondary reactor. Air is added in a burner, and the oxygen and methane react exothermically. The hot gas passes adiabatically through a catalyst bed and exits at approximately 1 000° C. The resultant synthesis gas contains CO, $CO_2$, $H_2$, $N_2$, $H_2O$ and small quantities of $CH_4$ and other unconverted hydrocarbons.

The synthesis gas is cooled and passed through first a high temperature shift converter operated at 320–350° C., then further cooled and passed through a low temperature shift converter. The combination converts almost all of the CO into $CO_2$ and $H_2$ by reaction with water. The gas is then treated to remove $CO_2$ using a suitable solvent A number of commercially available technologies can be utilised for this step. The solvent is regenerated by flashing, and the $CO_2$ is vented. Methanation is used as the final treatment step. In this unit, almost all of the remaining carbon oxides are reacted with $H_2$ to form methane and water. The water is removed using molecular sieve absorbers.

Some ammonia synthesis technology vendors (eg. Linde and KTI) do not use a secondary reformer as described above and use pressure swing adsorption (PSA) to separate $H_2$ from the other synthesis gas constituents. The $N_2$ is supplied from a cryogenic air separation unit. Overall efficiencies for this process are reported to be as good as conventional technology.

Synthesis gas comprising predominantly CO and $H_2$ can be used for the manufacture of liquid hydrocarbons utilising Fischer-Tropsch Synthesis. Hydrocarbons are typically produced by contacting synthesis gas with a preferred selective catalyst such as Co or Fe at 200–260° C. and 10–50 bar. Although it is known that the Fischer-Tropsch reaction can be performed in the presence of $N_2$, it is in general not preferred. In the process, $N_2$ acts as an inert gas that lowers the reactant partial pressures, and thus larger reactors or more catalyst is required. The selectivity to heavier hydrocarbons is also negatively affected by large concentrations of inert gases. As with ammonia synthesis, the synthesis gas for hydrocarbon production is typically produced from a natural gas feedstock utilising steam methane (tubular) reforming, autothermal reforming, or a combination of the two.

The process in which synthesis gas is produced for hydrocarbon production utilises a high purity $O_2$ stream in the reforming step rather than air, because the addition of inert gases (particularly $N_2$) is generally considered detrimental to the process economics. In stand alone Gas-to-Liquids (GTL) plants, nitrogen is an unused byproduct of the air separation step. GTL plants are very intensive oxygen users, with between 0.2 and 0.3 tonnes of oxygen consumed per barrel of product. Consequently between 0.5 and 0.7 tonnes of nitrogen per barrel of hydrocarbons is made available.

As with the ammonia synthesis catalyst, the Fischer-Tropsch catalyst is highly sensitive to poisoning by sulphur compounds and these have to be removed so that only extremely low levels remain to ensure economic catalyst life.

It is known in the art that under most conditions, the Fischer-Tropsch process requires a synthesis gas that contains $H_2$ and CO in a ratio at, or below, about 2.5, and more preferably at or below 2.0. This is because when certain catalysts are used, for example a Co catalyst, better selectivity for heavy hydrocarbons is achieved when the above ratio is at or below 2.0. Conventional steam reforming and autothermal reforming technologies produce synthesis gas at a ratio greater than this ideal. Various alternatives have been proposed to obtain the correct ratio. These involve recycling of $CO_2$ which can be extracted from various points in the synthesis loop or recycling the Fischer-Tropsch tailgas back to the reforming section. Such methods are useful not only because they reduce the $H_2/CO$ ratio, but also because they increase the overall carbon utilisation in the process.

Conversely, ammonia synthesis requires a very high $H_2/CO$ ratio. This is adjusted even further after the reforming section by using shift converters, which convert CO and water into $CO_2$ and $H_2$. The $CO_2$ is extracted using known methods and is vented to the atmosphere.

The ammonia synthesis process has been used in combination with a Fischer-Tropsch process commercially only in one case (by Sasol). In this process, the tail gas exiting the Fischer-Tropsch reactor is used as the source of hydrogen. After treatment of this gas to remove hydrocarbons, a portion is sent to a shift converter. $H_2$ is recovered and this is then reacted with $N_2$, obtained from a cryogenic oxygen plant, in the ammonia synthesis process. This process is useful when:

1) the synthesis gas enters the Fischer-Tropsch reactor with a $H_2/CO$ ratio greater than the stoichiometric ratio. The stoichiometric ratio is the ratio of $H_2$ used to CO used in the Fischer Tropsch reactor. When the synthesis gas enters the reactor with a high ratio, $H_2$ builds up and the tail gas contains a higher proportion of $H_2$ than the feedgas.

(A number of reactions influence the ultimate stoichiometric ratio, for example, the production of various hydrocarbons and the water gas shift reaction:

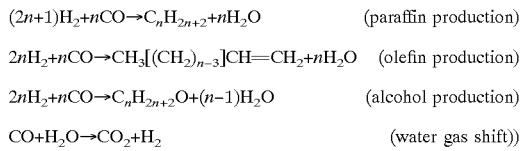

| | |
|---|---|
| $(2n+1)H_2+nCO \rightarrow C_nH_{2n+2}+nH_2O$ | (paraffin production) |
| $2nH_2+nCO \rightarrow CH_3[(CH_2)_{n-3}]CH=CH_2+nH_2O$ | (olefin production) |
| $2nH_2+nCO \rightarrow C_nH_{2n+2}O+(n-1)H_2O$ | (alcohol production) |
| $CO+H_2O \rightarrow CO_2+H_2$ | (water gas shift)) |

Each specific catalyst and the particular process conditions determine the ultimate stoichiometry of $H_2$ and CO utilisation because the relative rates of each of the reactions varies. In general, however, it is well known in the art that Fe based catalysts are active for the water gas shift reaction, while Co based catalysts are. not Thus the stoichiometric ratio for Co catalyst is close to 2.0, whereas it is somewhat lower for Fe based catalysts;

2) the conversion is low so that not all of the available $H_2$ is utilised and can thus be extracted from the tail gas for ammonia synthesis.

Modern GTL facilities are designed to primarily produce liquid fuel. This is achieved in a three step process involving a) synthesis gas generation, b) hydrocarbon synthesis and c) hydroprocessing. The processes are designed to be highly efficient with high conversions and good selectivity so that the liquid fuel product can compete economically with conventional fuels derived from crude oil. Thus in a modern GTL facility, the above Sasol process will not be suitable as options (1) and/or (2) above are not considered to be viable.

There therefore remains a need for optimising the conversion of natural gas to synthesis gas so that desired $H_2/CO$ ratios are obtained for use in both the production of hydrocarbons and the production of ammonia.

SUMMARY OF THE INVENTION

The present invention provides a novel way for overcoming problems in the operation of existing ammonia—Fischer-Tropsch integrated plants.

The present invention relates to an optimisation process for the production of hydrocarbons and ammonia that significantly reduces the capital and operating costs for the combined processes.

In particular, the present invention provides a process for combined hydrocarbon and ammonia production which reduces emission of $CO_2$ into the atmosphere. In the process, hydrogen is extracted from a reforming section of a hydrocarbon synthesis process rather than being extracted from the tail gas stream, and is then fed into an ammonia synthesis reactor. Previously, hydrogen necessary for ammonia synthesis was produced using shift reactions which also produced large amounts of $CO_2$, which were subsequently vented to the atmosphere. The hydrogen may be extracted from the reforming section by using known methods in the art.

According to a first aspect of the invention there is provided a process for converting natural gas to synthesis gas for the production of both hydrocarbons and ammonia, the process including the following steps:

extracting hydrogen from a synthesis gas in a hydrocarbon synthesis process prior to the synthesis gas entering a Fischer-Tropsch reactor; and feeding at least a portion of the extracted hydrogen into an ammonia synthesis process.

The hydrogen may be extracted from a reforming section of the hydrocarbon synthesis process until a $H_2/CO$ ratio of the synthesis gas is lower than or equal to a preselected value, the value typically being 2.5, and more preferably being 2.0 $CO_2$ may be removed from the synthesis gas prior to its entry into the Fischer-Tropsch reactor.

The synthesis gas exiting the reforming section may be split into at least two streams, the first stream entering the Fischer-Tropsch reactor and the second stream being sent to a hydrogen extraction unit. The synthesis gas may be divided into a hydrogen-rich stream and a hydrogen-poor stream in the hydrogen extraction unit, and at least a portion of the high purity hydrogen-rich stream may be fed into the ammonia synthesis process, thereby reducing or eliminating the danger of CO poisoning.

The hydrogen-poor stream may be returned to the hydrocarbon synthesis process or may be used as fuel gas. CO and/or $CO_2$ may be removed from the hydrogen-poor stem.

A portion of the Fischer-Tropsch tail gas may be returned to the reforming section of the Fischer-Tropsch process.

A combined air separation means may be used for both the hydrocarbon synthesis process and the ammonia synthesis process, and similarly a combined reforming section may also be used for both the hydrocarbon synthesis process and the ammonia synthesis process.

According to yet a further aspect of the invention, there is provided a combined hydrocarbon synthesis plant and ammonia synthesis plant, including means for extracting hydrogen from a reforming section of the hydrocarbon synthesis plant and feeding at least a portion of the extracted hydrogen into the ammonia synthesis plant. The hydrocarbon synthesis plant may be a Fischer-Tropsch plant.

Means for separating at least a portion of the synthesis gas into a hydrogen-rich stream and a hydrogen-poor stream prior to feeding at least a portion of the hydrogen-rich stream into the ammonia synthesis plant may also be provided.

The combined Fischer-Tropsch plant and ammonia synthesis plant may also include means for returning the hydrogen-poor stream to the reforming section of the Fischer-Tropsch plant.

The combined Fischer-Tropsch plant and ammonia synthesis plant may further include means for returning at least a portion of the Fischer-Tropsch tail gas to the reforming section.

Means for feeding at least a portion of the extracted hydrogen into a hydroprocessing section of the Fischer-Tropsch plant may also be provided.

According to yet a further embodiment of the invention there is provided a hydrocarbon produced according to the process described above.

According to yet a further embodiment of the invention there is provided ammonia produced according to the process described above.

The invention will now be illustrated further by way of the following non-limiting examples:

EXAMPLE 1

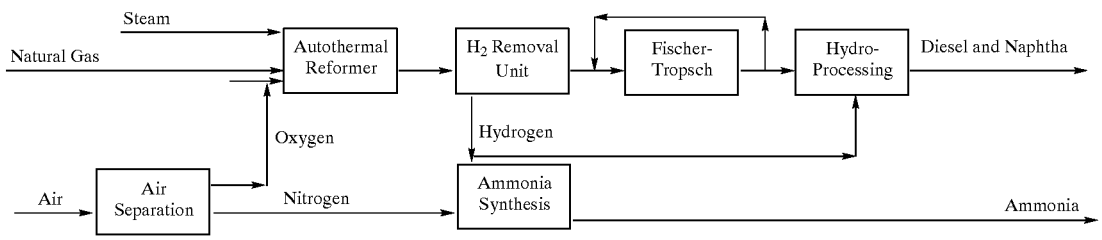

Natural gas is passed through one or more means of removing sulphur compounds from the gas so that the level of sulphur no longer poses a poisoning risk for either a Fischer-Tropsch or an ammonia synthesis catalyst. The desulfurized natural gas is then combined with oxygen and steam and reacted in an autothermal reformer. The oxygen is supplied from a cryogenic air separation facility. The reformer unit produces a synthesis gas with an $H_2/CO$ ratio of greater than 2.0, the actual ratio being determined by the steam/reformable carbon ratio, operating conditions and composition of the feed gas. A hydrogen extraction unit is placed on the exit stream from the reformer or a portion thereof so as to adjust the $H_2/CO$ ratio to a value desired for optimal hydrocarbon synthesis, typically below 2.1. The removal step may be accomplished using, for instance, pressure swing adsorption (PSA) or a membrane unit, or any other known method. Optimally, the $H_2$ extraction will be performed on a slip stream. A high purity $H_2$ product and a $H_2$ poor effluent stream are produced. The effluent stream may be recompressed and returned to the synthesis gas stream at any point in the loop or it may be used as fuel gas. The synthesis gas is then sent to a Fischer-Tropsch reactor that operates at a total conversion level above approximately 80%.

The excess hydrogen that has been removed above is further purified if required, compressed and sent to an ammonia synthesis reactor. Nitrogen, which is available at high purity from the cryogenic air separation unit is either compressed in gaseous form or more conveniently produced in liquid form and pumped to the appropriate pressure. The nitrogen is treated to remove trace quantities of oxygen, then combined with the hydrogen and also sent to the ammonia synthesis loop.

A plant of this type is used to produce 30 000 barrels per day (bpd) of liquid hydrocarbons and a further 1 000 tons per day of ammonia. Natural gas with the composition given in Table 1 is utilised for the purposes of this illustration. Process conditions may alter depending on the composition of natural gas in different situations. Process conditions will also alter depending on the relative quantites of ammonia and hydrocarbon products desired.

Table 2 compares the results of two individual plants operated at optimal conditions, one to give 30 000 bpd of liquid fuels and the other plant is used to produce 1 000 t/d ammonia, with a combined plant Plant 1 uses 300 000 $m^3{}_n/h$ of natural gas fed to an autothermal reformer operating with a steam/reformable carbon ratio of 0.6 and an exit temperature of 1 050° C. A $CO_2$ recycle is used to adjust the $H_2/CO$ ratio of the resulting synthesis gas to 1.90. The synthesis gas is fed directly into a Fischer-Tropsch synthesis plant after cooling and water knock-out. 30 000 bpd of liquid fuel is produced.

Plant 2 uses 28 500 $m^3{}_n/h$ of natural gas fed to a steam reformer operating with a steam/reformable carbon ratio of 4.0 and an exit temperature of 850° C. The steam reformer requires fuel gas to provide the heat required to drive the reaction. The resulting synthesis gas is cooled and transferred first to a high temperature shift reactor operating at 370° C., then to a low temperature shift reactor operating at 230° C. The gas is cooled and water is knocked-out from the stream. The dry gas is passed to a Benfield unit which removes the majority of $CO_2$. The gas is then passed to a methanation reactor which converts the remaining carbon oxides to $CH_4$. Finally, the $H_2$ rich gas is compressed and combined with $N_2$ from a cryogenic air separation plant and fed to an ammonia synthesis reactor, where 90% of the $H_2$ is converted. 1 000 t/d of ammonia is produced.

The combined plant utilises a combination of the above process schemes. 336 700 $m^3{}_n/h$ of natural gas is fed to an autothermal reformer operating with a steam/reformable carbon ratio of 0.9 and an exit temperature of 1 000° C. A similar quantity of recycled $CO_2$ is added to the feed gas as for the first plant. The resultant synthesis gas is cooled and a portion split off and transferred to a Pressure Swing Adsorption (PSA) unit. The resulting $H_2$ stream is greater than 99% pure. It is compressed and mixed with $N_2$ derived from a cryogenic air separation plant and transferred to an ammonia synthesis reactor, where 90% of the $H_2$ is converted to ammonia. 1 000 t/d of ammonia is produced. The majority of the offgas from the PSA is recompressed and returned to the main synthesis gas stream. The combined stream is again split, with a portion of the synthesis gas stream being sent to a Benfield unit where $CO_2$ is removed. The partially $CO_2$-depleted synthesis gas is sent to a Fischer-Tropsch synthesis plant 30 000 bpd of liquid fuel is produced.

TABLE 1

Natural gas composition used for purpose of illustrating the invention

| Component | Volume % |
| --- | --- |
| $CO_2$ | 1.5 |
| $CH_4$ | 89.5 |
| Inerts | 1 |
| $C_2$ hydrocarbons | 7.4 |
| $C_{3+}$ hydrocarbons | 0.6 |

TABLE 2

Comparison between stand alone plants and combined plant

| | Stand Alone Gas-to-Liquids Plant | Stand Alone Ammonia Synthesis | Plant 1 + Plant 2 | Combined Plant |
| --- | --- | --- | --- | --- |
| NG Feed ($m^3{}_n/h$) | 300 000 | 28 500 | 328 500 | 337 000 |

TABLE 2-continued

Comparison between stand alone plants and combined plant

| | Stand Alone Gas-to-Liquids Plant | Stand Alone Ammonia Synthesis | Plant 1 + Plant 2 | Combined Plant |
|---|---|---|---|---|
| Fuel Gas ($m^3_n/h$) [note 1] | 0 | 8 500 | 8 500 | 0 |
| Total NG Used ($m^3_n/h$) | 300 000 | 37 000 | 337 000 | 337 000 |
| $O_2$ Consumed (t/h) | 270 | 11 [note 2] | 281 [note 2] | 290 |
| $H_2$ Used For Ammonia Synthesis (kmol/h) | 0 | 4 085 | 4 085 | 4 085 |
| $N_2$ Used For $NH_3$ synthesis (kmol/h) | 0 | 1 362 | 1 362 | 1 362 |
| $NH_3$ Produced (t/d) | 0 | 1 000 | 1 000 | 1 000 |
| Liquid fuel Produced (bpd) | 30 000 | 0 | 30 000 | 30 000 |
| Total $CO_2$ Produced kmol/h [Note 3] | 0 | 1 467 | 1 487 | 1 218 |

[Note 1]: This includes only the additional fuel gas required to fire the tubular steam reformer.
[Note 2]: Although $O_2$ is not used in the reforming section, it is produced as a byproduct of the $N_2$ production. Approximately 11t/h of byproduct $O_2$ is produced.
[Note 3]: The production of $CO_2$ makes the comparison between conventional ammonia production and the increase in $CO_2$ production in the combined plant over the stand alone Gas-to-Liquids plant.

The advantages of the combined plant are:

scale economies can be used so that less expensive synthesis gas generation can be achieved;

an air separation plant for ammonia synthesis is not required;

the ammonia plant process scheme is very much simplified because pure hydrogen is produced in one step and no cleanup steps to remove carbon oxides is required. The carbon oxides are used in the Fischer-Tropsch unit; and 17% less $CO_2$ is consequently produced compared to a conventional ammonia plant.

Example 2 shows a slight modification of the process described in example 1.

EXAMPLE 2

Natural gas mixed with a recycle stream from a Fischer-Tropsch reactor is sent to the reforming section of a Fischer-Tropsch plant. The reforming section consists of a steam reformer followed by an autothermal reformer. The natural gas stream is split, with a portion entering the steam reformer, while the majority enters the autothermal reformer. Hot synthesis gas from the steam reformer mixes with the bypass natural gas before entering the autothermal reformer.

A hydrogen extraction unit is placed on the exit stream from the autothermal reformer or a portion thereof so as to adjust the $H_2/CO$ ratio to a value below 2. The synthesis gas is then sent to a Fischer-Tropsch reactor that operates at a total conversion level above 80%. Some of the Fischer-Tropsch tail gas is returned to the front of the reforming section. This can be utilised to further adjust the $H_2/CO$ ratio as well as increasing the carbon utilisation of the process.

The excess hydrogen that has been removed is further purified, compressed and sent to an ammonia synthesis reactor. Nitrogen, which is available at high purity from the cryogenic air separation unit is combined with the hydrogen and also sent to the ammonia synthesis loop.

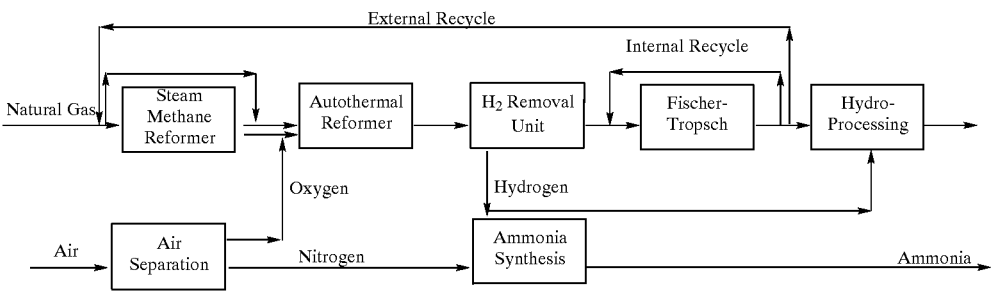

EXAMPLE 3

Natural gas mixed with a recycle stream from a Fischer-Tropsch reactor is sent to the reforming section of a Fischer-Tropsch plant. The reforming section consists of a steam reformer followed by an autothermal reformer. The natural gas stream is split, with a portion entering the steam reformer, while the majority enters the autothermal reformer. The synthesis gas from the steam reformer is cooled and sent to a shift reactor which converts most of the CO and $H_2$ into $CO_2$ and $H_2$. The $H_2$ is then separated from the other gases. The hydrogen poor offgas (consisting predominantly of $CO_2$) may be compressed and returned to the front end of the autothermal reformer. The split ratio between the steam reformer and autothermal reformer is adjusted so that the $H_2/CO$ ratio of the synthesis gas leaving the autothermal reformer is below 2.1. The synthesis gas is then sent to a Fischer-Tropsch reactor that operates at a total conversion level above 80%. Some of the Fischer-Tropsch tailgas is returned to the front of the reforming section. This can be utilised to further adjust the $H_2/CO$ ratio as well as increasing the carbon utilisation of the process.

The excess hydrogen that has been removed is fewer purified, compressed and sent to an ammonia synthesis reactor. Nitrogen, which is available at high purity from the cryogenic air separation unit is combined with the hydrogen and also sent to the ammonia plant.

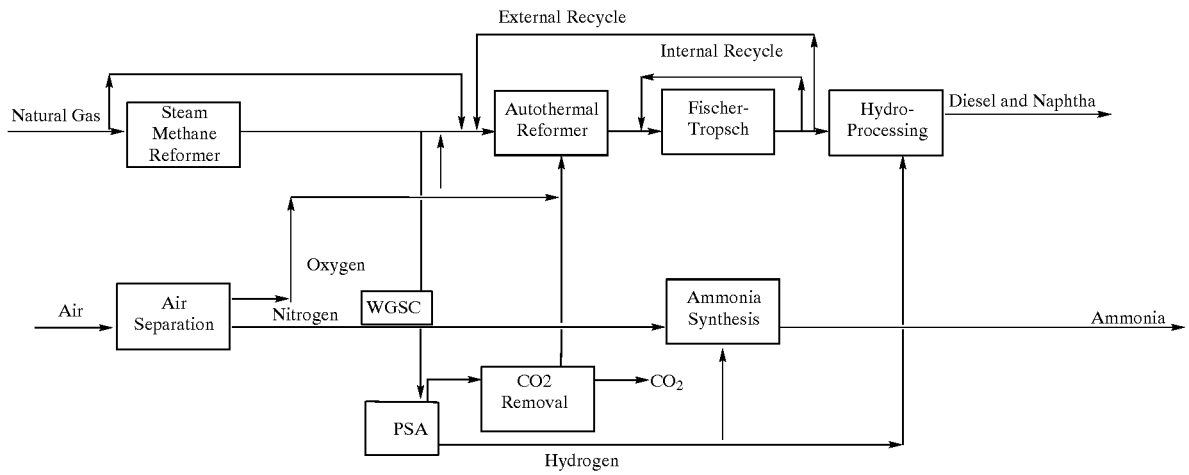

A plant of this type is used to produce 30 000 barrels per day (bpd) of liquid hydrocarbons and a further 1 000 tons per day of ammonia. Natural gas with the composition given in Table 1 of example 1 is again utilised for the purposes of this illustration. Process conditions may alter depending on the composition of natural gas in different situations. Process conditions will also alter depending on the relative quantities of ammonia and hydrocarbon products desired.

328 000 $m^3_n/h$ of natural gas is fed to the reforming section of a combined hydrocarbon synthesis and ammonia synthesis plant as exemplified above. 29 000 $m^3_n/h$ is sent to a steam reformer, while the rest bypasses the steam reformer. The majority of the product stream from the steam reformer is sent to a water gas shift converter (WGSC) operating at 230° C., which converts almost all of the CO into $H_2$ and $CO_2$ by reaction with water. The product stream is dried and sent to a hydrogen recovery unit. The offgas from the $H_2$ recovery unit is split, with approximately 50% passing through a $CO_2$ adsorption unit. The remaining stream is recompressed, if required, and mixed with the remaining natural gas. This, together with a recycle stream from the Fischer-Tropsch unit is fed into an autothermal reforming reactor. This reformer is operated at a steam/reformable carbon ratio of 0.6, and an exit temperature of 1 000° C. The product from this step is fed the Fischer-Tropsch reactor. Table 3 shows the results from this type of plant.

TABLE 3

Comparison between stand alone plants and combined plant

|  | Stand Alone Gas-to-Liquids Plant | Stand Alone Ammonia Synthesis | Plant 1 + Plant 2 | Combined Plant |
| --- | --- | --- | --- | --- |
| NG Feed ($m^3_n/h$) | 300 000 | 28 500 | 328 000 | 328 000 |
| Fuel Gas ($m^3_n/h$) [note 1] | 0 | 8 500 | 8 500 | 8 705 |
| Total NG Used ($m^3_n/h$) | 300 000 | 37 000 | 337 000 | 336 705 |

TABLE 3-continued

Comparison between stand alone plants and combined plant

|  | Stand Alone Gas-to-Liquids Plant | Stand Alone Ammonia Synthesis | Plant 1 + Plant 2 | Combined Plant |
| --- | --- | --- | --- | --- |
| $O_2$ Consumed (t/h) | 270 | 11 [note 2] | 281 [note 2] | 261 |
| $H_2$ Used For Ammonia Synthesis (kmol/h) | 0 | 4 085 | 4 085 | 4 085 |
| $N_2$ Used For $NH_3$ Synthesis (kmol/h) | 0 | 1 362 | 1 362 | 1 362 |
| $NH_3$ Produced (t/d) | 0 | 1 000 | 1 000 | 1 000 |
| Liquid Fuel Produced (bpd) | 30 000 | 0 | 30 000 | 30 000 |
| Total $CO_2$ Produced kmol/h [Note 3] | 0 | 1 467 | 1 467 | 1 352 |

[Note 1]: This includes only the additional fuel gas required to fire the tubular steam reformer.
[Note 2]: Although $O_2$ is not used in the reforming section, it is produced as a byproduct of the $N_2$ production. Approximately 11t/h of byproduct $O_2$ is produced.
[Note 3]: The production of $CO_2$ makes the comparison between conventional ammonia production and the increase in $CO_2$ production in the combined plant over the stand alone Gas-to-Liquids plant.

The advantages of this process scheme are that less oxygen is required for the combined plant than for even the stand-alone Gas-to-Liquid plant, with 7% less oxygen required than for the sum of the individual stand alone plants. Also 7% less $CO_2$ is emitted to the atmosphere compared with the two stand-alone plants. This translates to more than 40 000 tonnes fewer $CO_2$ emissions per annum.

The applicant believes that the invention is advantageous in that apart from the high total conversion obtained, substantial economic benefits also result for example:

1) a separate reforming section for an ammonia plant is not required;

2) $H_2$ can be produced in excess of the requirement of hydrocarbon synthesis, and the excess $H_2$ can be cost-efficiently used in ammonia production;

3) an $H_2$ steam is extracted from the synthesis gas stream and thus $CO_2$ which would be vented to atmosphere in a conventional ammonia facility remains in the it Fischer-Tropsch loop, and is further used to adjust the synthesis gas ratio to the desired value; and 4) conventional Fischer-Tropsch processes that aim to produce motor fuels additionally require a hydroprocessing section to upgrade the primary Fischer-Tropsch products into diesel. This requires a hydrogen source that incurs additional capital expenditure. However, the present invention does not require this additional hydrogen source. thus resulting in a substantial monetary saving. In addition, the operating pressure of the hydroprocessing section is greater than 70 bar, and the operating pressure of the ammonia synthesis loop is greater than 100 bar. Hydrogen can be removed after the second stage of the ammonia feed compressor and sent to the hydroprocessing section, thereby eliminating the expensive feed compressor from the hydroprocessing section of the GTL plant.

The capital and operating costs for the combined processes are therefore significantly reduced.

The invention is not limited to the precise constructional details as herein described.

What is claimed is:

1. A process for the production of hydrocarbons and ammonia, the process including the steps of:

by means of air separation means, separating air into oxygen and nitrogen;

in a reforming section, reacting natural gas, steam and oxygen from the air separation facility, to form synthesis gas;

in a hydrogen extraction unit, extracting hydrogen from at least a portion of the synthesis gas;

thereafter feeding the synthesis gas into a Fischer-Tropsch reactor in which hydrocarbons are produced from the synthesis gas, with the reforming section, the hydrogen extraction unit and the Fischer-Tropsch reactor forming part of a hydrocarbon synthesis process; and feeding at least a portion of the extracted hydrogen into an ammonia synthesis process together with the nitrogen from the air separation means, with the air separation means thus being a combined air separation means for both the hydrocarbon synthesis process and the ammonia synthesis process, and with the reforming section thus being a combined reforming section for both the hydrocarbon synthesis process and the ammonia synthesis process so that separate reforming sections for the hydrocarbon synthesis process and the ammonia synthesis process are not required.

2. A process as claimed in claim 1, wherein the hydrogen is extracted until a $H_2/CO$ ratio of synthesis gas fed to the Fischer-Tropsch reactor is lower than or equal to 2.5.

3. A process as claimed in claim 1, wherein the $H_2/CO$ ratio is lower than or equal to 2.

4. A process as claimed in claim 1, wherein only a portion of the synthesis gas is sent to the hydrogen extraction unit and is divided into a hydrogen-rich stream, at least a portion of which is fed into the ammonia synthesis process, and a hydrogen-poor stream.

5. A process as claimed in claim 4, wherein the hydrogen-poor stream is returned to the hydrocarbon synthesis process.

6. A process as claimed in 4, wherein the hydrogen-poor stream is used as fuel gas.

7. A process as claimed in claim 4, wherein CO and/or $CO_2$ are removed from the hydrogen-poor stream.

8. A process as claimed in claim 1, wherein at least a portion of $CO_2$ is removed from the synthesis gas stream prior to the synthesis gas stream entering the Fischer-Tropsch reactor.

9. A process as claimed in claim 1, wherein a portion of a Fischer-Tropsch tail gas is returned to the reforming section of the hydrocarbon synthesis process.

* * * * *